United States Patent [19]

Jensen et al.

[11] Patent Number: 4,825,711
[45] Date of Patent: May 2, 1989

[54] PROBE UNIT FOR AUTOMATIC DETERMINATION OF QUALITY PROPERTIES OF MEAT

[75] Inventors: Niels J. Jensen, Herlev; Michael N. Sorensen, Roskilde; Steen Halden, Fredensborg, all of Denmark

[73] Assignee: Slagteriernes Forskningsinstitut, Roskilde, Sweden

[21] Appl. No.: 93,418

[22] Filed: Sep. 4, 1987

[30] Foreign Application Priority Data

Sep. 5, 1986 [DK] Denmark .............................. 4247/86

[51] Int. Cl.$^4$ ............................................... G01J 3/46
[52] U.S. Cl. ................................................... 73/865.8
[58] Field of Search .................... 73/865.8, 866, 866.5, 73/432.1, 633, 634, 623; 356/72, 73, 381, 398, 402, 405, 445, 448; 250/338.1, 336.1, 215, 216, 224, 226, 234, 235; 33/141 R, 141 E

[56] References Cited

U.S. PATENT DOCUMENTS

| | | | |
|---|---|---|---|
| 3,435,231 | 3/1969 | Griffiths et al. | 356/398 |
| 3,614,230 | 10/1971 | Crawford | 356/72 |
| 3,643,508 | 2/1972 | Schneider | 73/866.5 |
| 3,753,405 | 8/1973 | Bryan, Jr. | 250/234 |
| 4,270,274 | 6/1981 | Hennessy | 356/381 |
| 4,387,592 | 6/1983 | Welker | 73/866.5 |
| 4,438,649 | 3/1984 | Gilman | 73/866.5 |
| 4,439,037 | 3/1984 | Northeved et al. | 356/402 |
| 4,577,411 | 3/1986 | Martin | 33/141 E |

FOREIGN PATENT DOCUMENTS

| | | | |
|---|---|---|---|
| 2804/78 | 6/1978 | Denmark . | |
| 5546/78 | 12/1978 | Denmark . | |
| 66836 | 12/1892 | Fed. Rep. of Germany | 33/141 E |
| 2000280 | 1/1979 | United Kingdom . | |
| 1576582 | 10/1980 | United Kingdom | 356/445 |

Primary Examiner—Stewart J. Levy
Assistant Examiner—Robert R. Raevis
Attorney, Agent, or Firm—Fleit, Jacobson, Cohn & Price

[57] ABSTRACT

A probe unit for automatic determination of quality properties in meat comprises an insertion probe with a measuring device, such as a light reflection meter, at a free end of the probe. A double-acting drive cylinder unit reciprocatingly moves the insertion probe and consists of an interior pipe surrounded by an outer impact resistant pipe. A tubular piston rod is reciprocatingly slidably arranged in the interior pipe. The piston rod extends through both ends of the interior pipe and has an overall length at least twice the length of its stroke. The front end of the piston rod serves as the insertion probe while the rear end of the piston rod carries or forms part of a position meter producing electric pulses indicative of the position of the light reflection meter with respect to the interior pipe. The position meter includes a signal generator with a toothed wheel engaging a toothed rack and generates pulses applied to a pulse counter. The signals from the measuring device represent the type and/or quality of the material in which the measuring device is present at any time. The probe unit is sturdy and reliable in operation and requires little space, in particular in transverse direction, and therefore is appropriate for incorporation in automatic systems with many probe units.

6 Claims, 1 Drawing Sheet

PROBE UNIT FOR AUTOMATIC DETERMINATION OF QUALITY PROPERTIES OF MEAT

BACKGROUND OF THE INVENTION

Pig slaughterhouses classify the individual slaughter animals to pay the pig producer in accordance with the quality of the animals supplied. Classification of slaughter hogs is determined by means of some meat and fat thickness measurements which an operator performs with a gun-lke instrument.

The instrument has a pointed probe which the operator inserts into the carcass at predetermined locations. During the passage into or out of the carcass the measuring means of the probe detect transition from one material to another, e.g. from meat to fat.

The detection may be based on different conductivity of the materials or on changed reflection of light.

The actual penetration depth of the probe in the procedure is determined by a reference plate which is movably positioned on the instrument and which constantly engages the surface of the carcass under the action of a spring. The plate is firmly mounted on the end of one or two slide rods acting on a position meter which is incorporated in the instrument. Thus, the meter provides a signal which represents the actual penetration depth of the probe with respect to the rind surface.

The probe and depth signals are coupled in a control unit to a measurement result for the meat and fat thickness. The results can be related to other parameters, such as weight, in a connected calculating unit so as to automatically provide a value of the so-called meat percentage. This determines the price categroy to be paid for a particular carcass.

The method described requires training of special classifying operators who must be able to operate the instrument correctly.

The measurement results are subject to some uncertainty, which is parly owing to the system and partly to the operator.

SUMMARY OF THE INVENTION

The invention concerns a probe unit and its object is to provide such a probe unit which lends itself to be mounted in an automatic measuring apparatus which can perform the measurements on the supplied carcasses necessary to determine the quality properties of these without assistance from an operator. Such probe units are to enable thickness measurements with good accuracy on all occurring types of carcasses, so as to provide reliable determination of the qualities of the individual caracasses. Since the apparatus is to accommodate a rather large number of probe units, e.g. ten, it is important that the individual unit is a compact and sturdy structure. In particular, the dimensions in the transverse direction should be as small as possible.

These requirements are satisfied by a probe unit according to the present invention. Thus, in this structure, the position meter can easily be kept within the transverse dimensions determined by the drive cylinder, and the simple structure makes the unit sturdy and reliable in operation.

The present probe unit makes it possible to determine meat and fat thickness on carcasses without any need for an operator, since a suitable number of probe units mounted in a frame can automatically perform the necessary measurements, controlled by a control unit.

When the probes are inserted into and/or extracted from the carcass, a plurality of associated values for the light reflection and the probe position may be provided by means of the light reflection as a function of the movement of the probe. The meat and fat thicknesses may be determined directly in a computer on the basis of the representation.

Thus, the probe unit of the invention is not vitiated by the errors which occur in connection with the known instruments and which are caused by wrong calibration of the zero point of the length meters and compression of meat and fat layers because of the engagement pressure of the reference plate.

The compact structure and simple operation of the probe unit permits construction of an automatic apparatus which can perform far more measurements during the allocated period of time than the instruments served by operators. Nevertheless, the risk of errors is relatively small, one reason being that the measurement is not dependent upon correct positioning of a reference plate, and the measuring method is relatively tolerant in respect of incorrect positioning of the probe. For example, bones and cartilage which the probe might hit will immediately manifest themselves in a series of constant position measurement results. Owing to the small force and inertia of the probe and the piston rod when they encounter these portions, there is no risk of broken probes which are left in the meat.

With more probe units it is also possible to perform so many thickness measurements on a carcass that it is even possible to classify the individual cuts of the carcass. Thus, the cuts need no longer be used in accordance with the classification of the carcass, but may instead be used according to their actual quality.

The light reflection measuring means used is sufficiently sensitive to be able to distinguish not only between fat and meat, but also between various meat qualities. It may e.g. be used for determining fat marbling or meat colour, thereby also giving information on cuts with a too high fat marbling or too light meat. Thus, it is possible in the same operation to obtain measurement results which determine the meat percentage of the carcass, while very specifically determining the usefulness of the cuts in the further processing.

It is moreover possible to perform automatic thickness measurements on cuts so that these may be sorted or processed in accordance with the meat and fat thicknesses measured. For example, the knife of trimming machines for loin cuts can be controlled accurately by the thickness measurements recorded in a measuring set-up to enable production of loins with a uniform thickness of fat or a thickness of fat determined by the fleshiness.

The position meter may be arranged in several ways. It may e.g. have a coil surrounding the piston rod, or a counter-coupled light detector may be provided, sensing a line division on the piston rod. A simple and reliable embodiment of the position meter is disclosed.

The reference means may e.g. be a potentiometer, but owing to the accuracy it is preferred that the signal generator is a pulse generator acting on a counter circuit.

The signal generator should be so arranged that it releases a pulse e.g. for each 0.1 mm displacement of the piston rod. Rotating pulse generators are useful for this purpose.

Preferably, the light reflection measuring means consists in a known manner of a light diode and a photo diode or transistor juxtaposed on a substrate with a partition between them, since this provides for a very fine detection of the transition between the various materials. The measuring means can operate in the region for visible light or in the infrared region. When monochromatic light or the like is used, the measuring means preferably operates in a wavelength region providing good contrast between areas with good quality properties, e.g. normal meat, and less valuable areas, e.g. fat or light meat. In the probe unit embodiment dislcosed, both the measuring means and the connecting lines are protected effectively.

The position meter and the rear part of the piston rod may expediently be protected against pollution by being surrounded by a housing. This housing may suitably form an elongation of and have the same length as a corresponding housing surrounding the cylinder. The probe with the measuring means is then the only exterior movable part of the probe unit, which is thus easy to mount and clean.

Owing to the movement of the reflection measuring means, the lines to it should be flexible to pass over materials tolerant to bending. This makes it even possible to establish durable line connections inside a pipe whose diameter just corresponds to the diameter of the cylinder. This can be done in that the flexible lines have been folded once and are secured to the end of the rod and the contact means, respectively, to be generally parallel with the piston rod inside the housing.

BRIEF DESCRIPTION OF THE DRAWINGS

The invention will be described more fully below with reference to the drawing, which shows an embodiment of the probe unit of the invention.

DESCRIPTION OF THE PREFERRED EMBODIMENT

Figure 1:
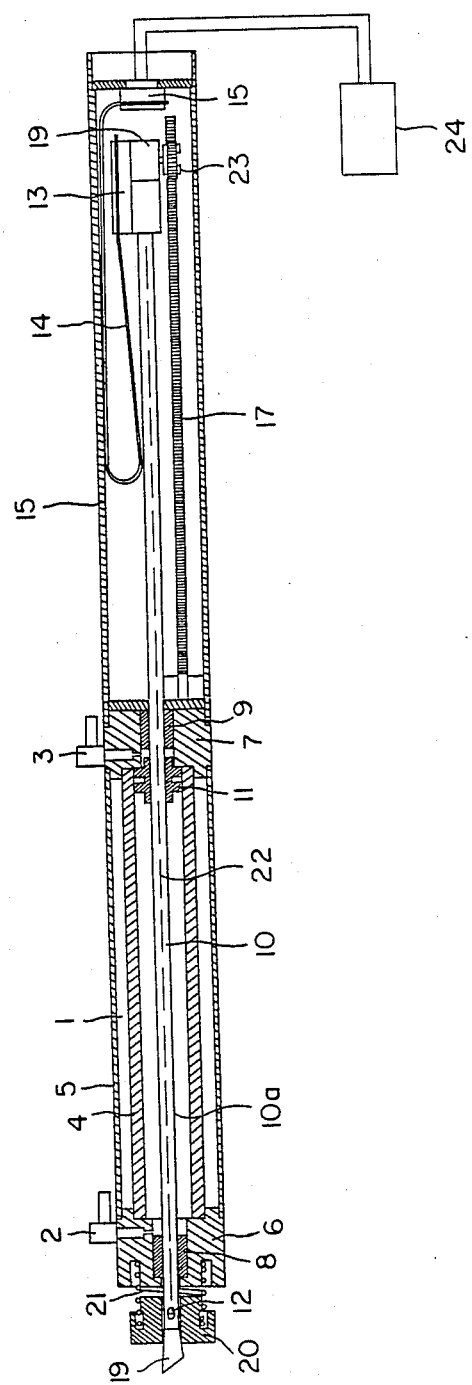

The probe unit is built around a double-acting pneumatic cylinder 1 with two connection nipples 2 and 3 for compressed air. The cylinder consists of an interior pipe 4 and is surrounded by an outer impact resistant pipe 5. Both pipes are secured between two end members 6 and 7, which are each provided with a gasket 8 and 9 through which a tubular piston rod 10 is arranged for sliding reciprocation under the action of a piston 11. As the drawing shows, piston rod 10 extends through both ends of interior pipe 4.

The piston rod has a window in which a light reflection measuring means 12 is bonded by means of clear resin. The reflection measuring means consists in a known manner of a light diode and a photo diode secured to a small plate. A wall is present between the light diode and the photo diode so that the photo diode does not receive light directly from the light diode, but just light which is reflected from materials outside the window.

Conventional electric wiring or lines 22, illustrated schematically in the drawing figure, are passed from the reflection measuring means are passed through the hollow piston rod to the right end of the rod, where they are connected with a printed circuit board 13 mounted on the rod and containing a pre-ampoifier for the photo diode. The printed circuit board is connected through bent flexible electric lines 14 with a contact means in the form of a plug socket 15 mounted on the end wall of a protective housing 16. Through this socket the probe unit may be electrically connected with equipment recording signals from the reflection measuring means and a position meter mounted in the housing 16.

This position meter consists of an elongated reference means in the form of a rack 17 secured to the end member 7 in parallel with rod 10 and a pulse generator 18 mounted on the end of the piston rod. The pulse generator has a shaft with a toothed wheel 23 running on the rack.

The free front end 10a of the piston rod serves as an insertion probe and is provided with a removable tip 19 having an inclined cutting edge whose greatest transverse dimension is greater than the diameter of the piston rod. It should be clear from the drawing FIGURE that the measuring means 12 is provided in the free end of insertion probe 10a. A ring-shaped white body 20 is placed around the insertion probe 10a of the rod and is affected by a spring 21 positioned between the body and the end member 6.

To avoid penetration of moisture and pollutants into the probe unit, there is provided narrow channels (not shown) leading from the small space directly below each of the nipples 2 and 3 into the space which is defined by the pipes 4 and 5. Likewise, a channel leads from the latter space into the space defined by the housing 16. Thus, a slight positive pressure is maintained in the cavity of the probe unit.

The probe unit of the invention is preferably used in large automatic systems for determination of the quality properties of carcasses, but the unit may also be used in automatic systems for determination of meat colour in loin cuts. A plurality of probe units is mounted in such systems by fixing the housing of the cylinder, the position meter housing or the like on frames suitable for the purpose. The frames may be provided with adjustment devices which position the probe units correctly with respect to the carcass or the cut, depending upon its size and shape.

After the frame with the probe units of the system has been positioned with respect to the carcass, the units are activated by means of a control system. Compressed air is automatically admitted to the right chamber of the cylinder through the nipple 3, thereby causing the piston 11 to move the rod 10 with the probe to the left. When the tip 19 meets the rind surface on the carcass, it cuts a slit through which the insertion probe 10a with the measuring means 12 can easily be introduced into the carcass.

The movement of the piston rod produces electric pulses in the pulse generator 18 because of the rotation of the toothed wheel in engagement with the rack 17. The pulses are applied via the flexible electric lines 14 to outer recording equipment with a pulse counter 24 of known construction whose display is indicative of the position of the rod. It should thus be clear that the position meter formed by rack 17 and pulse generator 18 meters the position of measuring means 12 with respect to pipe 4. If the time interval between the counter pulses exceeds a predetermined threshold value, the probe has encountered bones or cartilage, and the control system causes the compressed air supply to be switched to the left chamber of the cylinder so that the probe immediately returns to the starting position.

Normally, the probe does not encounter bones or cartilage, and the piston will complete its movement until it reaches the top far left position in the cylinder 1. In this position, the probe has passed through the inner side of the carcass so that the reflection measuring means is again disposed in air.

The control system then switches the compressed air supply to the left chamber of the cylinder so that the probe is withdrawn from the carcass. During the movement of the piston rod to the right, the pulse generator 18 again generates electric pulses affecting the counter of the recording equipment. From the foregoing, it should be clear that the double-acting pneumatic cylinder reciprocatingly moves insertion probe 10a into an out of a caracass under the action of the compressed air.

Each time the counter display is counted up by 1, a reflection measurement is performed and the reflection value is stored. This provides for a set of associated values of reflection and position for each 0.1 mm movement of the rod 10 to the right. First, the reflection measuring means registers air which gives no reflection, then meat which has a certain reflection, and fat which has a strong reflection, and finally again air which is perceived black.

The reflections measured are converted to symbols indicative of air, fat or meat by introduction of suitable reflection limit values in the recording equipment. The equipment may then calculate the thickness measures for meat and fat by means of the associated position values. The measures are passed via a data transmission line to a main computer, which, depending upon the program, prints thicknesses, meat percentage and/or class and optionally controls equipment labelling the carcasses and the cuts in accordance with their qualities. The equipment may also control sorting systems which transport the carcasses and the cuts to the relevant processing locations in the slaughterhouse. Here, the cuts, etc., can be processed fully automatically or semi-automatically in accordance with the recordings, and e.g. the knife of a subsequent trimming apparatus can be controlled in response to the fat thickness recorded.

If desired, also reflection and position measurements may be performed during the insertion of the probe into the carcass.

It is also possible to detect by means of the recorded reflection values whether the tip 19 is still in position. Just before the piston reaches its bottom position, the tip 19 engages the body 20 and carries the body to the bottom position shown. In this position, the reflection measuring means registers the white colour of the body. If the tip is absent, the body maintains its rest position at the end of the spring 21 when the piston moves to the bottom position. The measuring means 12 will then just register air in the bottom position, which the recording system can convert to a signal indicating that a tip has possibly been left in the carcass.

We claim:

1. A probe unit for automatic determination of quality properties in meat comprising:
    an insertion probe
    a measuring means in a free end of said insertion probe,
    a double-acting drive cylinder unit for reciprocatingly moving said insertion probe, said double-acting drive cylinder unit including a pipe,
    a piston rod arranged for sliding reciprocation in said pipe and extending through both ends of said pipe and having a overall length at least twice the length of its stroke, the piston rod having a front end forming said insertion probe and a rear end,
    a position meter, located at said rear end of said piston rod, producing electric signals indicative of the position of the measuring means with respect to the pipe.

2. A probe unit according to claim 1, wherein said position meter comprises an elongated reference means firmly mounted in parallel with said piston rod and a signal generator disposed on the rear end of the piston rod cooperating with said elongated reference means.

3. A probe unit according to claim 2, and further comprising: a pulse counter, and wherein the elongated reference means is a toothed rack, and the signal generator has a toothed wheel engaging the toothed rack and adapted to generate signals in the form of pulses applied to said pulse counter.

4. A probe unit according to claim 3, and further comprising:
    a plug socket on an end wall of said probe unit connected to said pulse counter, and
    electric wiring extending in an axially arranged hollow space inside the piston rod from the measuring means to said signal generator, and also extending from said signal generator to said plug socket in the form of flexible lines with sufficient flexibility to accommodate reciprocation of said signal generator.

5. A probe unit according to claim 1, and further comprising:
    a tubular housing firmly connected with said double-acting drive cylinder, surrounding the position meter and the rear end of the piston rod.

6. A probe unit according to claim 5, and further comprising:
    a contact means firmly mounted in an end wall of the tubular housing, and
    a flexible electric connection between said position meter and said contact means.

* * * * *